(12) United States Patent
Kaneko et al.

(10) Patent No.: US 7,239,817 B2
(45) Date of Patent: Jul. 3, 2007

(54) DEVICE FOR IDENTIFYING TYPES OF SHEET MATERIALS

(75) Inventors: Norio Kaneko, Atsugi (JP); Takehiko Kawasaki, Atsugi (JP); Naoaki Maruyama, Atsugi (JP)

(73) Assignee: Canon Kabushiki Kaisha, Tokyo (JP)

( * ) Notice: Subject to any disclaimer, the term of this patent is extended or adjusted under 35 U.S.C. 154(b) by 91 days.

(21) Appl. No.: 10/535,837

(22) PCT Filed: Dec. 26, 2003

(86) PCT No.: PCT/JP03/16930

§ 371 (c)(1),
(2), (4) Date: May 20, 2005

(87) PCT Pub. No.: WO2004/059296

PCT Pub. Date: Jul. 15, 2004

(65) Prior Publication Data

US 2006/0016996 A1    Jan. 26, 2006

(30) Foreign Application Priority Data

Dec. 26, 2002  (JP) .............................. 2002-376132
Dec. 19, 2003  (JP) .............................. 2003-422763
Dec. 26, 2003  (WO) ....................... PCT/JP03/16930

(51) Int. Cl.
*G03G 15/00* (2006.01)
(52) U.S. Cl. ...................................... 399/45; 73/12.13
(58) Field of Classification Search .................... 399/45
See application file for complete search history.

(56) References Cited

U.S. PATENT DOCUMENTS

| 4,970,895 | A | 11/1990 | Houghton et al. ............ 73/159 |
|---|---|---|---|
| 4,976,138 | A | 12/1990 | Benninghoff et al. ........... 73/73 |
| 6,097,497 | A | 8/2000 | McGraw .................... 358/1.12 |
| 6,158,287 | A | 12/2000 | Satake et al. ................. 73/835 |
| 7,114,848 | B2* | 10/2006 | Kaneko ...................... 374/142 |
| 2003/0053089 | A1* | 3/2003 | Nojiri et al. ................. 358/1.9 |
| 2003/0053090 | A1* | 3/2003 | Nojiri et al. ................. 358/1.9 |
| 2005/0271403 | A1 | 12/2005 | Kaneko et al. ............... 399/44 |
| 2006/0016996 | A1 | 1/2006 | Kaneko et al. .......... 250/339.1 |
| 2006/0054842 | A1 | 3/2006 | Kawasaki et al. ..... 250/559.04 |

OTHER PUBLICATIONS

Ito et al., "Piezoelectricity", J. Webster (e.). Wiley Encyclopedia of ELectrical and Electronics Engineering, 1999, John Wiley & Sons, Inc., pp. 479-490.*
International Search Report.

* cited by examiner

*Primary Examiner*—David M. Gray
*Assistant Examiner*—David A Blackshire
(74) *Attorney, Agent, or Firm*—Fitzpatrick, Cella, Harper & Scinto

(57) ABSTRACT

A device for identifying types of sheet materials has a detecting unit for detecting information regarding moisture of a sheet material; external force applicator for applying an external force to the sheet material; information obtaining unit for obtaining information according to a force that is attenuated by the presence of the sheet material when the external force is applied to the sheet material by the external force applicator; and a judging unit for identifying the type of the sheet material based on the information obtained from the detecting unit and the information obtained from the information obtaining unit.

11 Claims, 14 Drawing Sheets

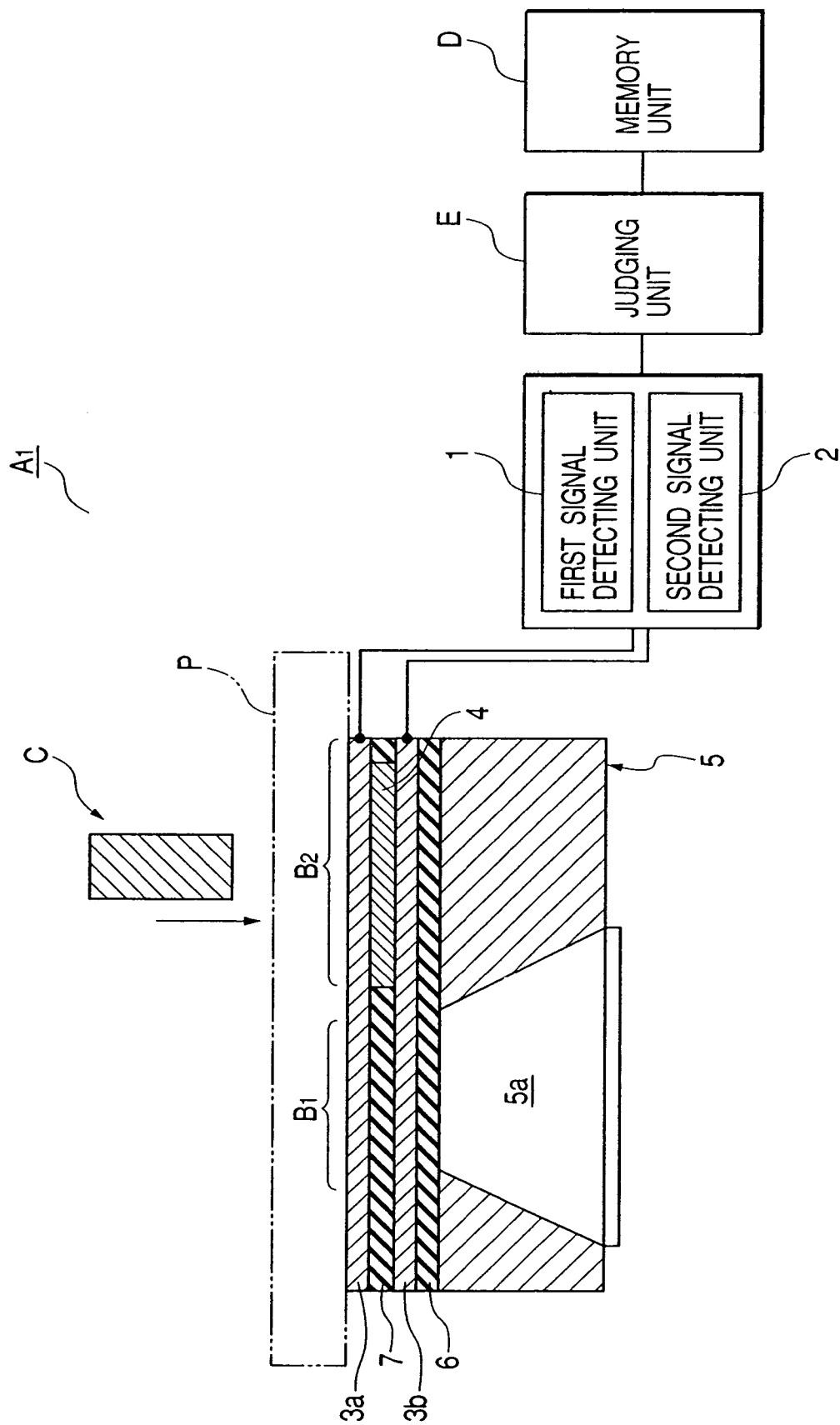

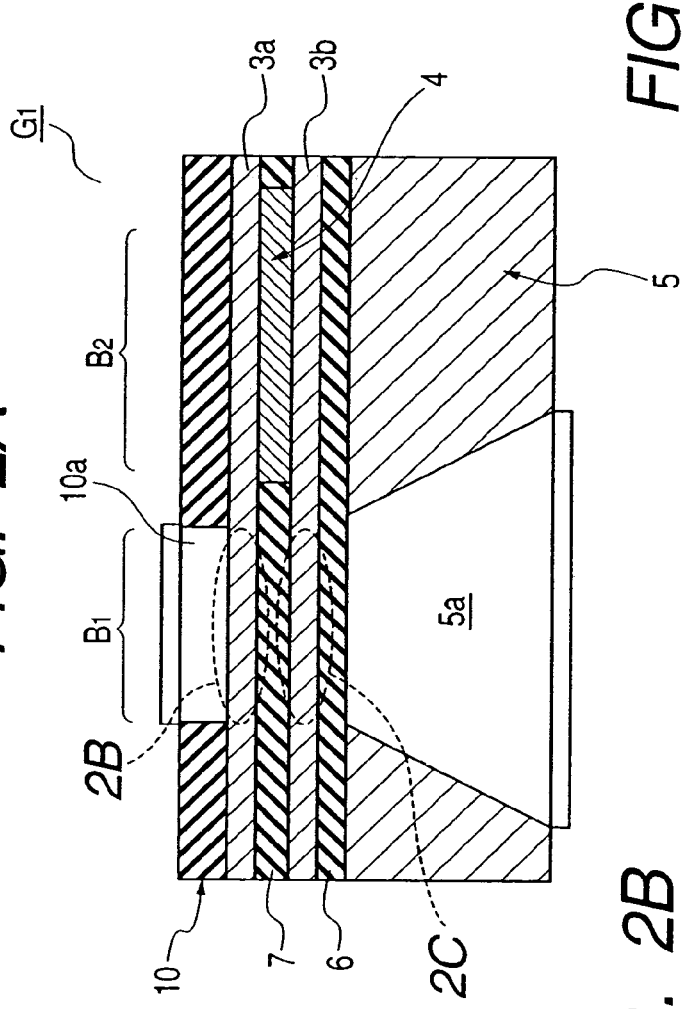
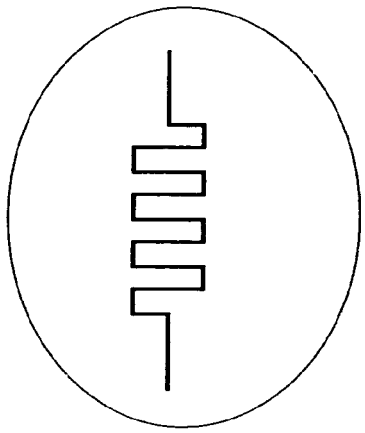
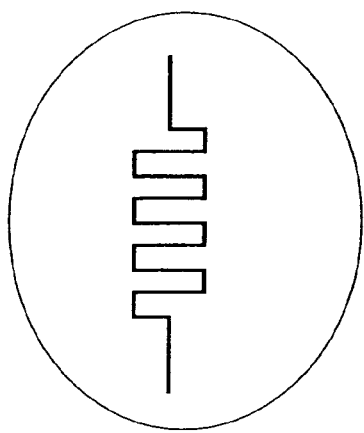

DEVICE FOR IDENTIFYING TYPES OF SHEET MATERIALS

TECHNICAL FIELD

The present invention relates to a device for identifying types of sheet materials.

BACKGROUND ART

Information detecting devices for detecting information of sheet materials have recently been attracting attention in various technical fields.

An example of those devices is disclosed in U.S. Pat. No. 6,097,497, in which a sheet material is marked in advance with a number code or symbol (hereinafter the method is referred to as marking method) and a sensor provided in a printer reads the number code and other information to set the optimum printing mode.

In this marking method, information that sheet materials can carry is limited to the kind that will not change after marking, such as the name of the manufacturer of the sheet material and the sheet material size.

Sheet materials in general are changed in water content by an environmental change (a change in humidity of atmospheric gas), and properties (for example, Young's modulus and other mechanical properties) of individual sheet material are varied depending on its water content. The marking method is incapable of detecting the water content of sheet materials and therefore cannot detect accurate sheet material information.

Also, it is impossible to obtain information from an unmarked sheet material with the marking method to begin with.

DISCLOSURE OF THE INVENTION

The present invention has been made in view of the above, and an object of the present invention is therefore to provide an information detecting device that can detect accurate information of sheet materials.

According to the present invention, a device for detecting information of a sheet material is characterized in that the device has a detecting unit for detecting information regarding moisture of a sheet material and information obtaining means for detecting a response of the sheet material to an external force applied to the sheet material, and information of the sheet material is detected based on the information obtained from the detecting unit and the information obtained from the information obtaining means.

BRIEF DESCRIPTION OF THE DRAWINGS

FIG. 1 is a sectional view showing an example of a structure of a device according to the present invention.

FIG. 2A is a sectional view showing an example of the structure of the device according to the present invention; and FIGS. 2B and 2C are enlarged plan views of electroconductive members at portions circled by dotted lines in FIG. 2A.

BEST MODE FOR CARRYING OUT THE INVENTION

Figure 3C:
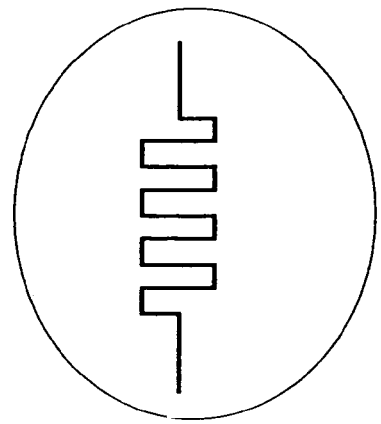
FIGS. 3B and 3C are enlarged plan views of electroconductive members at portions circled by dotted lines in FIG. 3A.

An embodiment of the present invention will be described below with reference to FIGS. 1 though 7.

The device according to the present invention is denoted by Symbol $A_1$ in FIG. 1. The device $A_1$ has a detecting unit $B_1$ for detecting information regarding the moisture of a sheet material P and information obtaining means $B_2$ for detecting a response (mechanical-physical properties, mechanical properties) of the sheet material P to an external force applied to the sheet material P, and is structured to detect information about the sheet material P based on these detection results.

In this specification, "mechanical properties" mean Young's modulus (bend and/or compression), basis weight ($g/m^2$), density, paper thickness, coarseness (smoothness), etc. irrespective of whether the sheet material P is formed from a single material or is a laminate of plural materials. "Information about sheet materials" means information about the mechanical properties described above, the water content, and types and classes of sheet materials, sizes of sheet materials, number of sheet materials, number of remainder of sheet materials, whether or not sheet materials are double fed, and the remaining amount of sheet materials. What the term "sheet material" means is varied depending on the use of the device. If the device is used in a printer or a copying machine, for example, "sheet material" means a sheet of plain paper, recycled paper, coated paper, glossy paper, OHP, or the like.

The information detecting means $A_1$ according to the present invention preferably has an external force applying unit C for applying an external force to the sheet material P in order that the information obtaining means $B_2$ detects a response (repellence or absorption) of the sheet material P that has received the external force.

Moreover, the information detecting means $A_1$ according to the present invention is preferably provided with a first signal detecting unit 1 for detecting a signal of the detecting unit $B_1$ and a second signal detecting unit 2 for detecting a signal of the information obtaining means $B_2$ (details thereof will be described later).

Furthermore, the information detecting means $A_1$ according to the present invention preferably has memory unit D for storing data of the moisture and mechanical properties (dependency on mechanical properties and the water content of sheet materials, and necessary information such as paper product number) of various sheet materials (sheet materials that are likely to be used), and a judging unit E for judging the type of a sheet material based on detection results of the detecting unit $B_1$ and the information obtaining unit $B_2$ and the data in the memory unit D. The judging unit E preferably judges the type of a sheet material based on signals from the first signal detecting unit 1 and the second signal detecting unit 2.

Symbol C denotes an external force applying unit; 3a, 3b, an electroconductive member (electrode), respectively; 4, a metal oxide; 5, substrate; 5a, a nicked portion of the substrate; 6, 7, an insulating film, respectively.

Given below is a description of the detecting unit $B_1$.

The detecting unit $B_1$ may be a unit that detects the moisture of the sheet material P or the humidity of the surroundings (the humidity of atmospheric gas), or may be a unit that detects both. Alternatively, the detecting unit $B_1$ may detect the humidity of atmospheric gas and then calculates from the result the moisture of the sheet material P.

Preferably, the detecting unit $B_1$ has an electroconductive member 3a and detects information regarding the moisture of a sheet material and the humidity of atmospheric gas from a change in electric resistivity of the electroconductive member 3a (a difference between the electric resistivity of the electroconductive member 3a being away from the sheet material P and the electric resistivity of the electroconductive member 3a being in contact with or in the vicinity of the sheet material P). In short, humidity detection in this case utilizes electric properties of the electroconductive member which allow moisture in the surroundings (an object that is in contact with the electroconductive member or atmospheric gas) to change the electric resistivity of the electroconductive member. The first signal detecting unit 1 mentioned above is desirably connected to the electroconductive member 3a to measure a change in electric resistivity of the electroconductive member 3a.

The electroconductive member 3a shown in FIG. 1 is in direct contact with the sheet material P, but it is not imperative for the electroconductive member 3a to be in contact with the sheet material P. For instance, in the device $G_1$, the electroconductive member 3a and the sheet material P may be kept at a given distance from each other as shown in FIG. 2A by forming an insulating film 10 on a surface of the electroconductive member 3a and opening a hole portion 10a in the insulating film 10 to allow the electroconductive member 3a to face the sheet material P at the hole portion 10a. The same symbols in FIG. 2A as those in FIG. 1 show the same members in FIG. 1. FIGS. 2B and 2C are enlarged plan views of electroconductive members 3a and 3b, respectively, at the portion of FIG. 2A surrounded by dotted line. The respective electroconductive members have a zig-zag shape to obtain their length more. The electroconductive member 3a in this structure can also detect the humidity of atmospheric gas (air) in the space between the sheet material P and itself (namely, the hole portion 10a) and the water content of the sheet material P can be obtained from the detection result. If data is prepared in advance by a similar measurement method and stored in the memory D, it is possible to reduce influence on detection accuracy. In the case where the insulating film 10 is provided, the electroconductive member 3a is covered, thus reducing the exposed area of the electroconductive member 3a as well as influence of the humidity in atmospheric gas (influence on the detection result). In addition, the temperature can be obtained from a change in electric resistivity (by measuring the electric resistivity for electroconductive members 3a and 3b both). With the correlation between the temperature and the electric resistance, the relative humidity can be calculated from a difference between the upper electroconductive member 3a and the lower electroconductive member 3b measured by the first signal detecting unit 1. Moreover, covering the electroconductive member 3a with the insulating film 10 as described above saves the electroconductive member 3a from wear which is caused by contact with the sheet material P. In the device $G_2$, the hole portion of the insulating film 10 may have a porous substance 11 as shown in FIG. 3A. Here, the electroconductive members include not only a portion that is layered on a metal oxide but also a wiring portion for capturing an electric signal from the three-layer structure portion. To measure the electric resistance, the electroconductive member may be smaller in thickness and width than its surroundings or may have a zigzag or other irregular shape. The same symbols in FIG. 3A as those in FIG. 1 show the same members in FIG. 1.

Figure 3A:
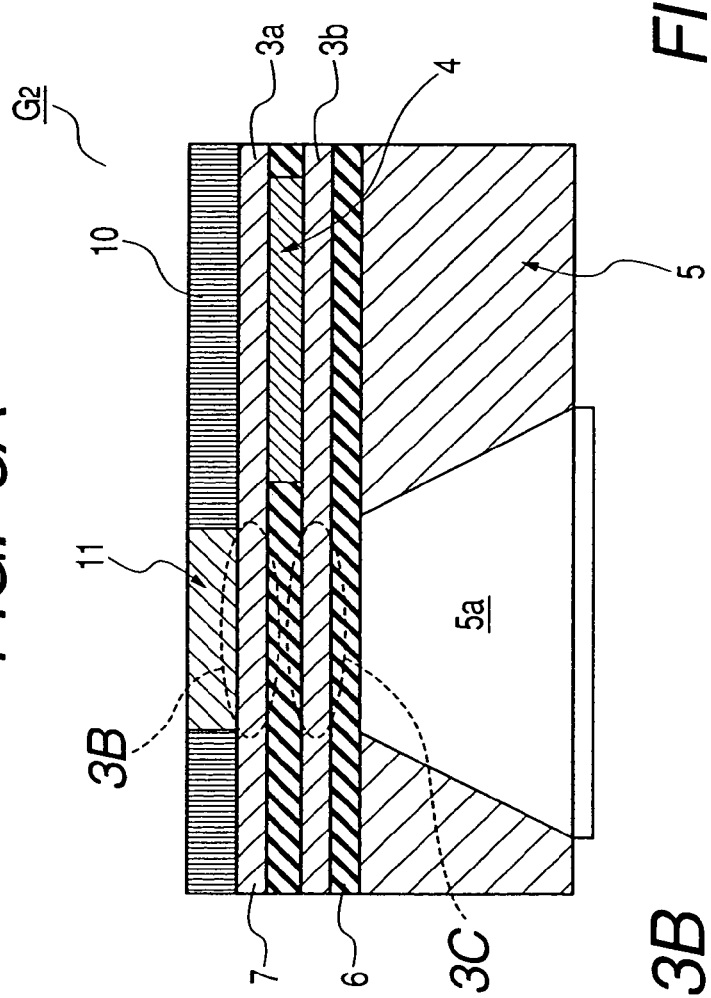
FIG. 3A is a sectional view showing an example of the structure of the device according to the present invention.
Figure 3B:
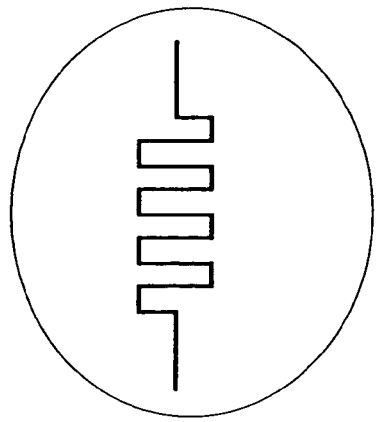

FIGS. 3B and 3C are enlarged plan views of electroconductive members 3a and 3b, respectively, at the portions of FIG. 3A surrounded by dotted line. The respective electroconductive members have a zig-zag shape to obtain their length more.

The external force applying unit C is described next.

Examples of external forces applied by the external force applying unit C include an impact force and an oscillating external force (transmission of a mechanical displacement of desired frequency to the sheet material).

Figure 6:
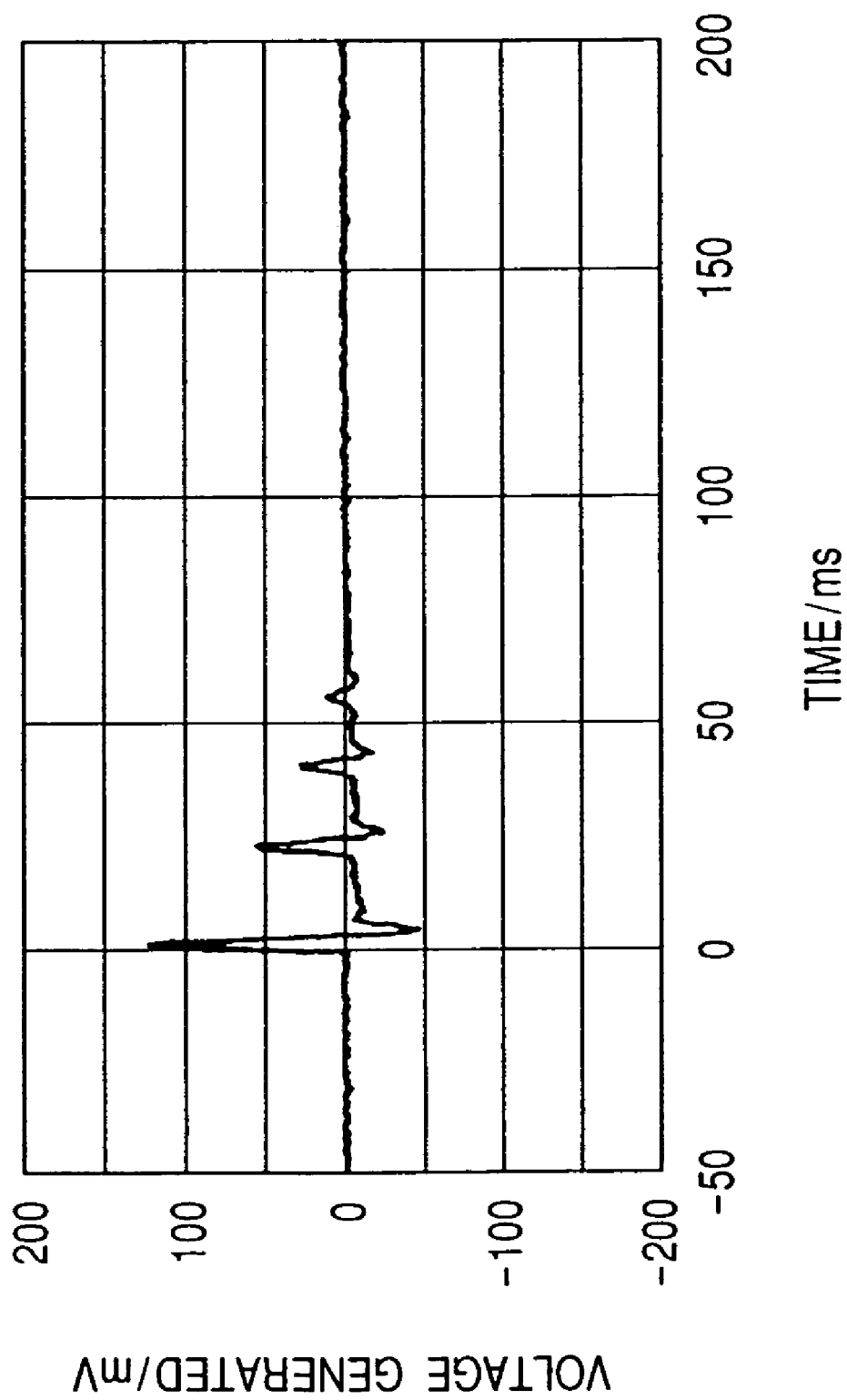
FIG. 6 is a waveform chart showing an example of a detection signal when an impact force is applied to a sheet material by an external force applying unit.

Examples of methods to generate an impact force include: a method in which a member having an appropriate weight is let free-fall, a method utilizing a spring force; a method utilizing an electromagnetic force driven at an arbitrary frequency; a method in which a rotary motion of a motor or the like is converted into a linear motion; and a method in which oscillation of a piezoelectric element is used to make a substance of desired shape to collide against a sheet material. The impact force thus generated may be applied once or plural times. Regularly repeated impact at an arbitrary frequency is also employable. In applying the impact force plural times, the impact intensity may be varied and the sheet material may be impacted in different places. In utilizing free fall or in similar cases, one fall naturally causes repeated impacts (in FIG. 6 showing the waveform of a signal generated in free fall, four impacts are observed) and, from the time interval between one impact from another, mechanical properties can be measured. In this case, the time interval can be obtained by counting the interval between the n-th impact (n is an integer equal to or larger than 1) and the m-th impact (m is an integer equal to or larger than 2 and satisfies m>n) with the initial impact from free fall set as the first impact. Alternatively, the recoil period may be obtained by generating a given pulse from the n-th impact to the (n+1)-th impact and counting the number of clock pulses that are generated in an AND circuit of the given pulse and an external clock pulse of known frequency.

Figure 11:
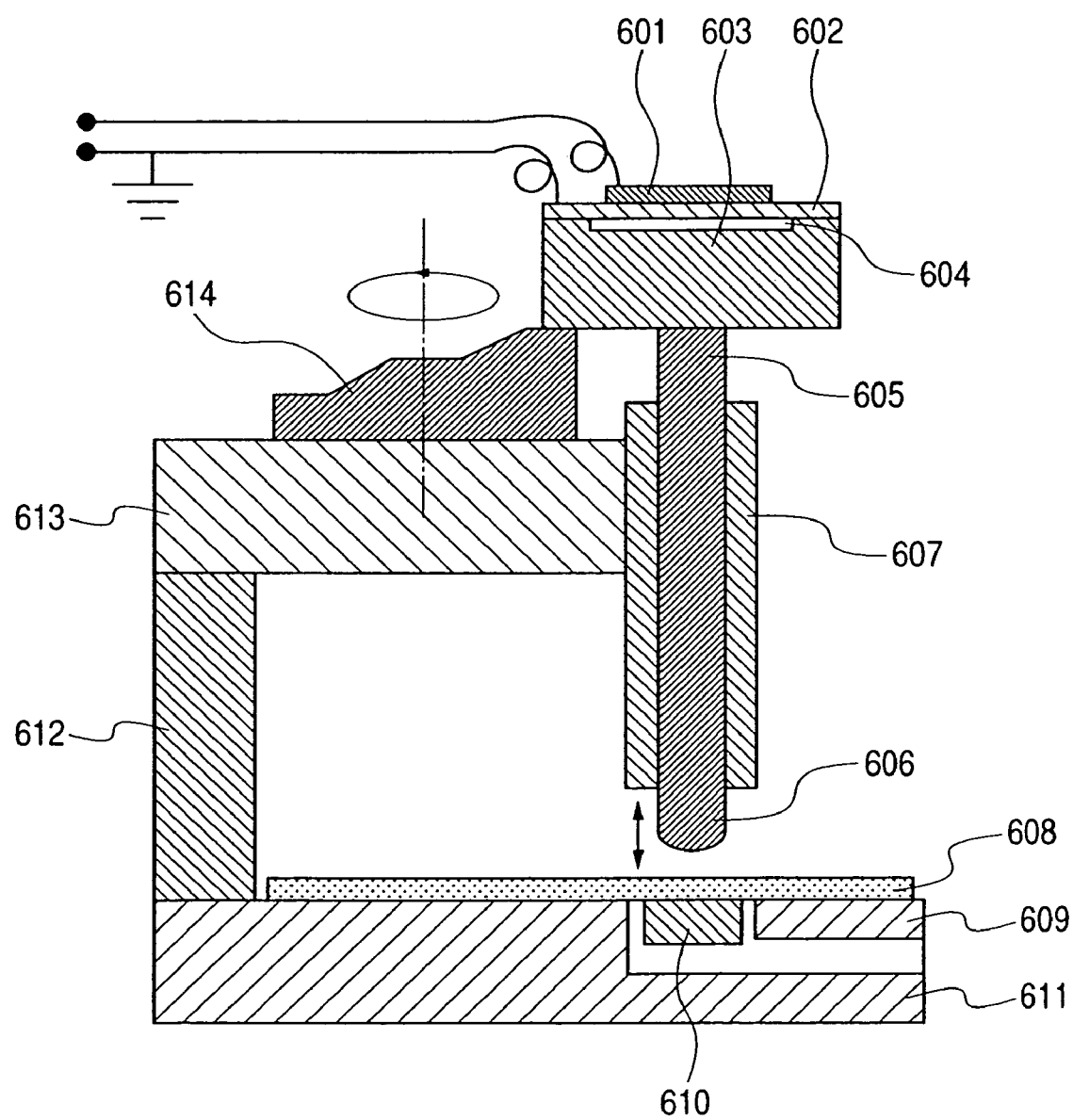
FIG. 11 is a sectional view showing an example of a structure of an external force applying unit.

The external force applying unit may have a structure shown in FIG. 11. In FIG. 11, the external force applying unit has contact members 603, 605 and 606 supported to move freely and come into contact with a sheet material 608 and a drive source 614 for driving the contact member 606, and the information obtaining means has an elastic member 602 mounted to the contact members 603, 605 and 606 and a deformation amount sensor unit 601 for detecting the deformation amount of the elastic member 602. This structure allows the information obtaining means to detect a response of the sheet material 608 based on the deformation amount of the elastic member 602 which is detected by the deformation amount sensor unit 601 when the contact members 603, 605 and 606 are driven by the drive source 614 to collide against the sheet material 608. The member 614 is driven and rotated by a not-shown motor to thereby move the member 603 up and down. Denoted by Symbol 609 is a sheet material supporting member and 611 represents a hole portion in the supporting member. 612 and 613 denote arms and 607 represent a guide for the contact member 605. Denoted by 604 is a concave portion for allowing the elastic member 602 to deform. Denoted by 610 is a member for defining movement distance and may be the same as 609. Generally, the member 610 has a planar or curved surface which is in contact with the sheet material. The member 610 is preferably movable up and down.

On the other hand, in order to oscillate a sheet material, the external force applying unit is preferably composed of: a frequency generating circuit for generating a signal of arbitrary frequency; an oscillation generating unit for converting a signal from the frequency generating circuit into oscillation of the same frequency; and an oscillation transmitting unit that is in contact with a sheet material to transmit oscillation from the oscillation generating unit.

The external force may be applied from a vertical direction (normal line direction) with respect to the sheet material P as shown in FIG. 1, or from a horizontal direction, or from an oblique direction. One or more than one types of external forces may be applied.

There is a possibility that a sheet material is deformed before an external force is applied thereto, or is vibrated during transportation. For such cases, the device of the present invention may have means for fixing a sheet material while an external force is applied to the sheet material and signals are detected by the first and second detecting means. The fixing means may use pressure or gravity to fix a sheet material. A sheet material can be fixed at one point or plural points. There is no limitation on means for generating pressure or gravity and any mechanical, electrical or magnetic means is employable.

The information obtaining means $B_2$ is described next. The description here deals with a case in which a metal oxide is used to form the information obtaining means.

Preferably, the information obtaining means $B_2$ is composed of a metal oxide 4 and the electroconductive members 3$a$ and 3$b$ to detect a response to the external force from a change in voltage of the metal oxide 4.

The metal oxide 4 is preferably a ferroelectric material, a pyroelectric material, or a piezoelectric material, so that the piezoelectric characteristic of the material is utilized to detect a response of a sheet material to an external force applied.

The electroconductive members 3$a$ and 3$b$ described above are preferably arranged to sandwich the metal oxide 4 forming a pair. The second signal detecting unit 2 described above is connected to the electroconductive members 3$a$ and 3$b$, allowing the second signal detecting unit 2 to measure a change in voltage of the metal oxide 4 (a voltage generated between the electroconductive members, a frequency component of a voltage generated, or the like).

Figure 4:
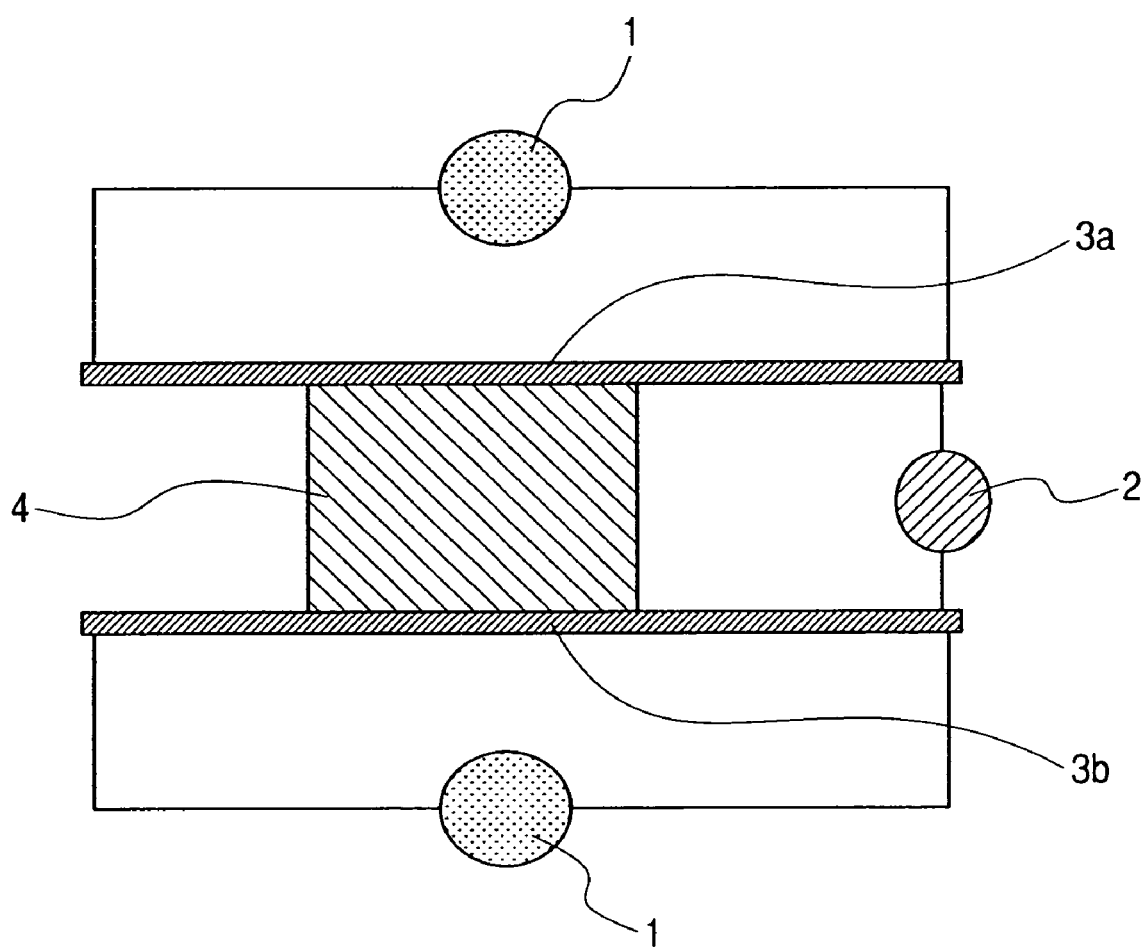
FIG. 4 is a schematic diagram showing a connection example of a first signal detecting unit and a second signal detecting unit.

Now a supplementary description is given on the first signal detecting unit 1 and the second signal detecting unit 2. The first signal detecting unit 1 is preferably connected to the electroconductive members 3$a$ and 3$b$ separately as shown in FIG. 4, so that the electric resistivity of the electroconductive members 3$a$ and 3$b$ can be measured separately. A difference in electric resistivity between the electroconductive member 3$a$ and the electroconductive member 3$b$ measured by the first signal detecting unit 1 is used to obtain the water content of the sheet material P. On the other hand, the second signal detecting unit 2 is preferably connected between the electroconductive member 3$a$ and the electroconductive member 3$b$ as shown in FIG. 4.

A sheet material has two Young's moduli, bending and compression. In the device of the present invention shown in FIG. 1, the Young's modulus that indicates compression is reflected when the second signal detecting unit is in contact with a sheet material whereas a signal reflecting the compressive Young's modulus and the Young's modulus that indicates bending both is detected when the second signal detecting unit is not in contact with a sheet material. To measure the bending Young's modulus alone, the external force applying unit and the second signal detecting unit are unitarily incorporated to obtain a structure that allows a sheet material to be bent but not compressed. Whether the second signal detecting unit is brought into contact with a sheet material, or whether the external force applying unit and the second signal detecting unit are integrated or not may be determined depending upon the usage of the device.

The detecting unit $B_1$ and the information obtaining means $B_2$ may be unitarily built or may be separately built and supported by the same base (denoted by Symbol 5). In the former case where the detecting unit $B_1$ and the information obtaining means $B_2$ are unitarily built, it is preferable to construct the information obtaining means $B_2$ from the metal oxide 4 and the electroconductive members 3$a$ and 3$b$ as described above and to let the electroconductive member of the detecting unit $B_1$ double as one of the electroconductive members of the information obtaining means $B_2$.

A specific example of this case (in which the detecting unit $B_1$ and the information obtaining means $B_2$ are unitarily built and supported to the same substrate (a plate-like base)) is described below referring to FIG. 1.

An insulating film 6 and the electroconductive member 3$b$ are arranged on a substrate 5 that is partially cut off (the nicked portion is denoted by 5$a$). The metal oxide 4 is formed in a part of a surface of the electroconductive member 3$b$ and an insulating film 7 is formed on the rest of the surface of the electroconductive member 3$b$. Then the electroconductive member 3$a$ is formed to cover the metal oxide 4 and the insulating film 7. In this structure, the three-layer structure portion B2 where the metal oxide 4 is sandwiched between the electroconductive members 3$a$ and 3$b$ forming a pair functions as the information obtaining means while the electroconductive members 3$a$ and others in the nicked portion 5$a$ function as the detecting unit B1. The first signal detecting unit 1 is connected to the electroconductive member 3$a$ and to the electroconductive member 3$b$, so that a change in electric resistivity of each electroconductive member can be measured. The first signal detecting unit 1 measures the electric resistivity before and after the electroconductive member 3$a$ is brought into contact with the sheet material P to measure the absolute water content from the difference between the measured electric resistivity levels (a change in electric resistivity which accompanies a contact with the sheet material P). An analytical curve is made in advance for the relation between the absolute water content and the electric resistivity. The nicked portion 5a of the substrate is provided to reduce the calorific capacity and thus increase the moisture detection speed. However, forming a nicked portion is not inoperative.

The external force applying unit C in FIG. 1 is an impact member that applies an impact force by dropping on the sheet material P. The information obtaining means $B_2$ shown in FIG. 1 is placed on the side opposite to the external force applying unit C (in other words, below the sheet material P) to detect absorption of the external force by the sheet material P. Alternatively, the information obtaining means $B_2$ and the external force applying unit C may be placed on the same side of the sheet material P and, in this case, the information obtaining means $B_2$ detects the resilience of the sheet material P against the external force. The information obtaining means $B_2$ may detect either absorption or repellence of power, or both.

In order to give the detecting unit $B_1$ high resolution of detecting a change in electric resistivity, it is desirable to shape a part of the detecting unit $B_1$ accordingly. The detecting unit $B_1$ in FIG. 1 employs the meander structure (see the enlarged plan views in FIGS. 2B and 2C). However, the shape is not limited thereto and other arbitrary shapes can be employed or the objective may be also achieved by varying the width or thickness of the electroconductive members. The electroconductive member 3a and the electroconductive member 3b may have the same shape (planar shape) or different shapes.

Figure 5:
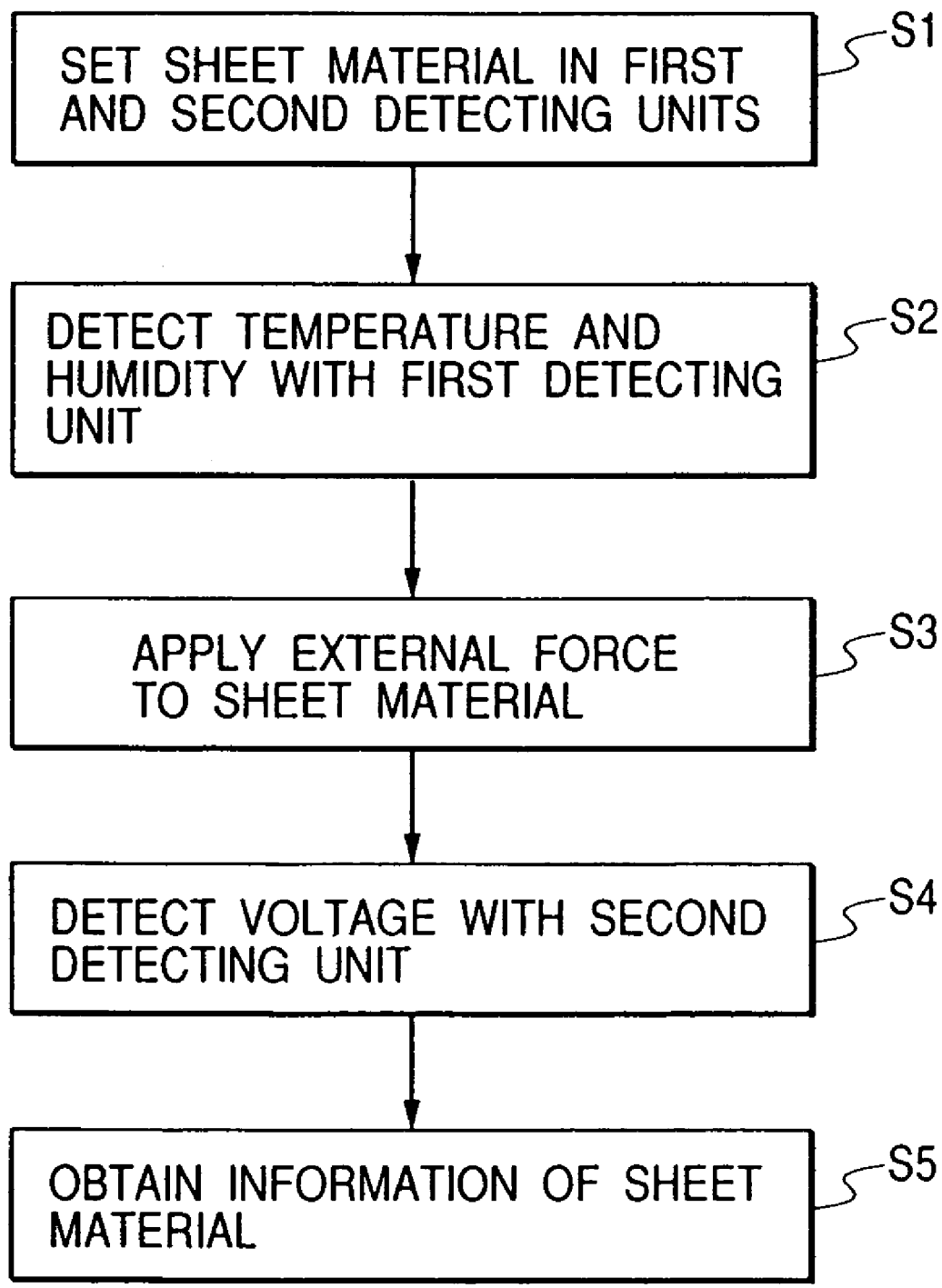
FIG. 5 is a flow chart illustrating an information detection procedure.

A detection procedure is described next with reference to FIG. 5.

First, the sheet material P is set in the detecting unit $B_1$ and the information obtaining means $B_2$ (Step S1). The detecting unit $B_1$ measures a change in electric resistance before and after the sheet material P is set. The detection result is compared with data in the data table to determine the humidity and temperature of the sheet material (Step S2).

Next, the external force applying unit C applies an external force to the sheet material P (Step S3). The application of the external force generates electric charges in the metal oxide 4 of the information obtaining means $B_2$ and the voltage thereof is detected. FIG. 6 is a waveform chart showing an example of a detection signal of the case when an impact force is applied to a sheet material by the external force applying unit C. Extracted from the waveform are the voltage peak value, a frequency component, a differential component, the time interval between voltage peaks, and the like. Then the judging unit E obtains mechanical properties (including Young's modulus, paper thickness, density, surface roughness) of the sheet material P based on the above voltage information. From the above temperature and humidity information and the data stored in the memory unit D, information of the sheet material P is obtained.

During this detection procedure, the sheet material P may be transported to the detecting unit $B_1$ and the information obtaining means $B_2$ by a transporting device (a roller or the like). It is also possible to take the opposite way and the detecting unit $B_1$ and the information obtaining means $B_2$ may be brought toward the sheet material P that is placed in a given location.

Described next is an image forming apparatus according to the present invention.

An image forming apparatus according to the present invention comprises: the device described above; an image forming unit for forming an image on a first sheet material (meaning a sheet material on which an image is formed by the image forming apparatus, this applies to the following description); a first sheet material transporting unit for transporting the first sheet material to the image forming unit; an image control unit for controlling image formation conditions based on information from the above-described information detecting device.

If necessary, the image forming apparatus according to the present invention may comprise: an image reading unit for reading an image of a second sheet material that is an original; a second sheet material transporting device for transporting the second sheet material to the image reading unit; a second storage unit for storing the second sheet material; a first storage unit for storing the above-described first sheet material; and a third storage unit for storing the first sheet material after an image is formed on the first sheet material. Instead of having the image reading unit, image data (electronic data) may be inputted to the image forming-apparatus from a personal computer or the like.

The above-described image forming apparatus may identify the type and the like of the first sheet material (whether the sheet material is transported normally or not, and the size and position of the sheet material) before the first sheet material is transported to the image forming unit, or may identify the type and the like of the second sheet material (whether the sheet material is transported normally or not, and the size of the sheet material) before the second sheet material is transported to the image reading unit, or may identify the first sheet material and the second sheet material both. In this case, the detecting unit $B_1$ is placed at some point in the transportation path to the first storage unit or the image forming unit whereas the information obtaining means $B_2$ is placed at some point in the transportation path to the second storage unit or the image reading unit. In this way, a high quality image can be formed.

Transportation errors refer to sheet materials being stuck to one another and transported together (so-called double feeding), and a sheet material not being transported at all.

The device preferably obtains information about a sheet material after the judging unit E consults the data in the memory unit D as described above. When the judging unit E cannot access the data of the memory unit D for some reason, an alarm may be displayed to indicate what kind of error has taken place. If data of a sheet material that is a detection object is not found in the memory unit D, necessary data is added to the archive of the memory unit D as the need arises. In the case where different types of sheet materials are to be detected in succession (when various sheet materials are mixed into a pile), one way to identify the mixed sheet materials is to measure mechanical properties alone immediately before image formation, store the measurement results in the memory unit D temporarily, and make the identification of the randomly mixed sheet materials by comparison with the temporarily stored data.

The information obtaining means $B_2$ detects mechanical properties of a sheet material as described above and, therefore, is also capable of finding out whether or not a sheet material is at a given position (the position where the information obtaining means $B_2$ is located). When a sheet material is not at the given position, an external force of the external force applying unit C is applied directly to the electroconductive member 3a instead of through a sheet material, whereby it can be detected that there is no sheet material.

Based on the same principle, the size and position of a sheet material and whether or not sheet materials are double fed can be detected by arranging plural information obtaining means $B_2$ and detecting the presence or absence of a sheet material at each information obtaining means $B_2$.

Examples of the image forming apparatus described above include copying machines, printers, and FAX machines.

Figure 7:
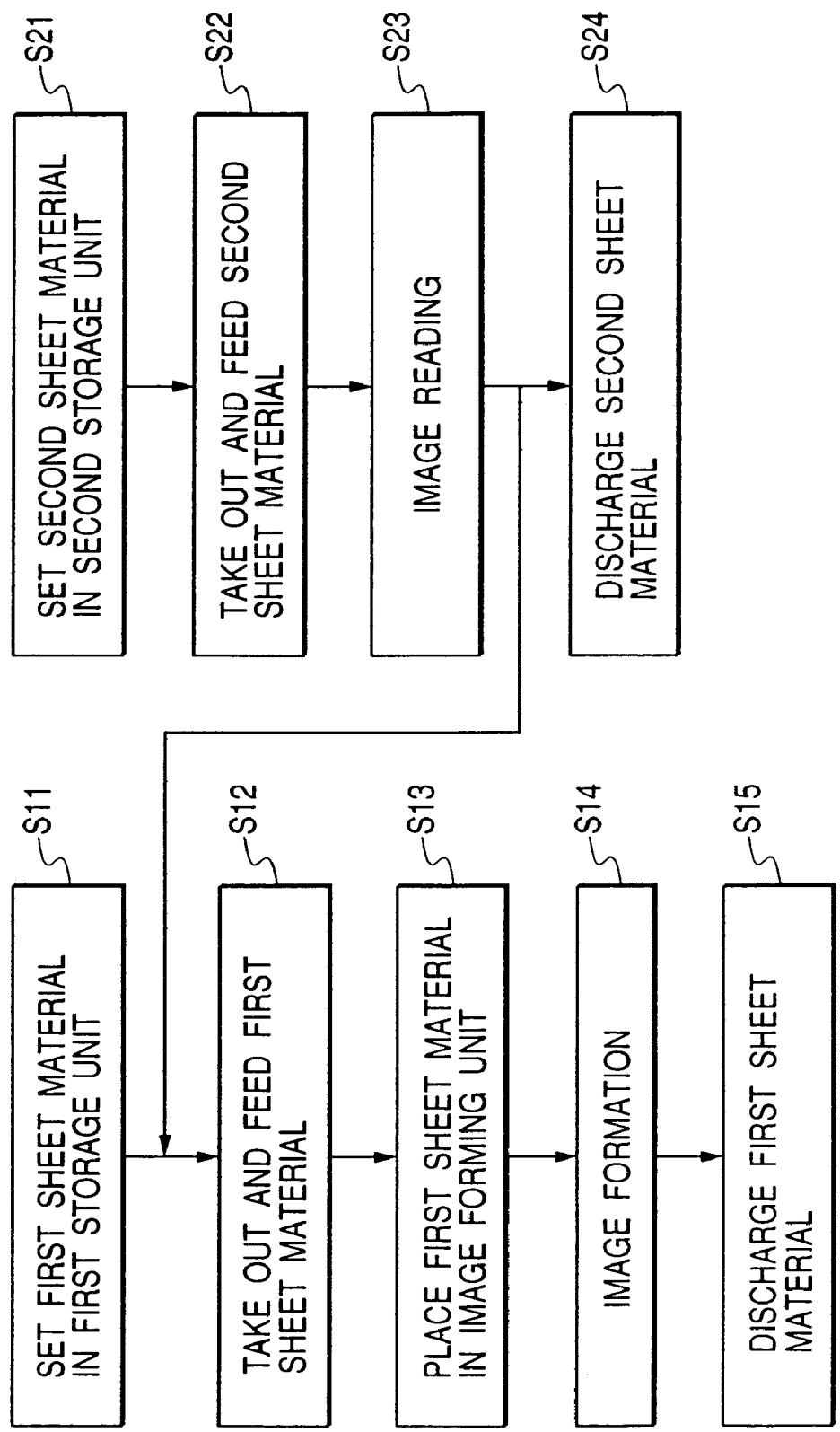
FIG. 7 is a flow chart illustrating an image forming procedure that an image forming apparatus follows.

Next, an image forming procedure is described with reference to FIG. 7.

The first sheet material is set in the first storage unit (Step S11 in FIG. 7) and the second sheet material is set in the second storage unit (Step S21). In this state, an operator performs a given operation such as depressing a switch button to start transportation of the second sheet material to the image reading unit where an image of the second sheet material is read (Steps S22 and S23). Meanwhile the first sheet material is transported to the image forming unit, where an image is formed on the first sheet material (Steps S12, S13 and S14). Then the first sheet material and the second sheet material are discharged (Steps S15 and S24).

Detection of the first sheet material (for example, identification of product number of the recording paper) is carried out during the period from Step S11 through Step S13 whereas detection (for example, detection of transportation error of the original) of the second sheet material takes place during the period from Step S21 through S23. Image formation conditions (in the case of an ink-jet printer, for example, the type of ink used, the size of an ink drop ejected, and all other information necessary to image formation) are determined based on these detection results and then an image is formed.

The description given next is about effects of this embodiment.

According to this embodiment, the water content as well as mechanical properties of sheet materials can be detected and therefore accurate sheet material information is obtained.

Another effect is that, unlike the conventional marking method, there is no need to mark sheet materials in advance and accordingly a wider range of sheet materials can be detected.

Hereinbelow the present invention will be described through specific embodiments.

EXAMPLE 1

In this example, a sheet identifying device (information detecting device) having a structure as shown in FIG. 1 was manufactured.

The metal oxide 4 was formed from $PbZrTiO_3$ (Zr/Ti=35/65) (hereinafter abbreviated as PZT) and Pt was used for the electroconductive members 3a and 3b. To improve the adhesion between the metal oxide 4 and the electroconductive members 3a and 3b, Ti (not shown in the drawing) was interposed between the metal oxide and the electroconductive members. The insulating films 6 and 7 were formed from $SiO_2$ and single crystal silicon was used for the substrate 5.

The external force applying unit C was structured as follows: the external force applying unit C was made of stainless steel (SUS). The tip of thereof is a hemisphere that was 3 mm in diameter and 6.6 g in weight. The external force applying unit C could be moved up and down by a not-shown device and was let free-fall when applying an external force. Note that the tip of the external force applying unit C may be planar instead, if there is no fear of scarring a sheet material. The height of fall and the mass of the external force applying unit C, which influence the force of impact, can be chosen freely as long as a sheet material is not damaged. The external force applying unit C may be formed from other material than stainless steel. A surface of the external force applying unit may be coated.

In manufacturing the device, the insulating film 6 with a thickness of 1 μm and the lower electroconductive member 3b with a thickness of 200 nm were formed first by sputtering on a surface of the substrate 5. A portion of the electroconductive member 3b that was not brought in contact with the PZT 4 was patterned to have a meander structure (see the enlarged plan views in FIGS. 2B and 2C). Thereafter, the PZT 4 was formed by sputtering to a thickness of 3 μm and was patterned by photolithography. The insulating film 7 was formed to the same thickness of 3 μm in a portion where the PZT 4 was removed. Then the upper electroconductive member 3a was formed to a thickness of 200 nm. The insulating film 7 and the electroconductive member 3a were both formed by sputtering. The upper electroconductive member 3a was patterned by photolithography to overlap with the lower electroconductive member 3b. The area of the PZT 4 should be larger than the area of the bottom of the external force applying unit C, and was set to 4 mm×5 mm in this example.

The electric resistivity of the upper electroconductive member 3a was measured before the sheet material P and the upper electroconductive member 3a came into contact with each other. Then a sheet of ink-jet recording paper LC 301 or GP 301 (a product of Canon Kabushiki Kaisha) was set on the upper electroconductive member 3a. It was found from the result obtained by measuring the electric resistivity that the temperature of the sheet material P was 25.6° C. At this point, the electric resistivities of the upper and lower electroconductive members 3a and 3b were measured to reveal that there was a 5.2% change in electric resistance of the upper electroconductive member and a 5.3% change in lower electroconductive member before and after the sheet material was brought into contact with the electroconductive member (this applies to LC 301 and GP 301 both). The humidity of the sheet material was obtained through comparison with a correlation table which was prepared in advance to show the correlation between the humidity and a change in electric resistivity; the humidity was 53.8% before the contact and was 53.9% after the contact.

Next, the external force applying unit C was dropped from a height of 2.5 mm onto the sheet material P. The voltage waveform generated between the electroconductive members upon impact on LC 301 is shown in FIG. 6. The external force applying unit C was let free-fall and bounced, generating four voltage peaks. The first peak voltage was 135 mv. When the sheet material P was GP 301, the first peak voltage was 109 mv.

The thickness and density for each of the sheet materials were obtained in advance using a micrometer and an electronic scale. The sheet material LC 301 had a thickness of 0.086 mm and a density of 0.93 g/cm$^3$ whereas GP 301 had a thickness of 0.195 mm and a density of 0.84 g/cm$^3$.

The level of voltage generated in the metal oxide 4 reflected the impact absorption amount of the sheet material. Accordingly, the LC 301 which was thinner generated high voltage and the high density of LC 301 raised the voltage level. Sheet material types were made detectable by utilizing such mechanical properties.

According to this example, the water content of a sheet material could be detected and therefore detailed sheet material information could be obtained.

EXAMPLE 2

Figure 8:
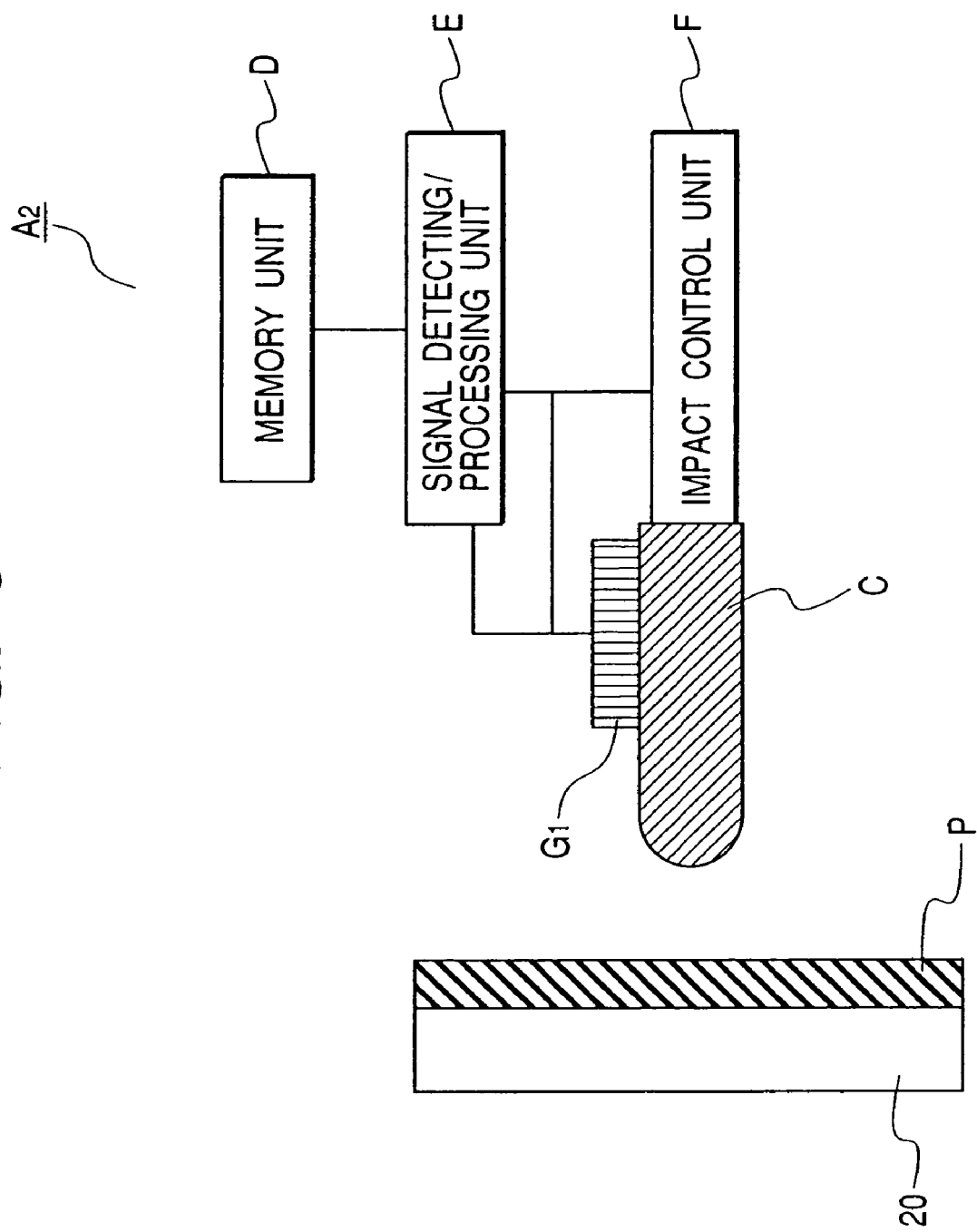
FIG. 8 is a sectional view showing an example of the structure of the device according to the present invention.

In this example, a sheet identifying device (information detecting device) $A_2$ having a structure shown in FIG. 8 was manufactured.

A media sensor $G_1$ for detecting the humidity and mechanical properties of the sheet material P was structured as shown in FIG. 2A. In FIG. 2A, the insulating film 10 was formed on a surface of the upper electroconductive member 3a, and the hole portion 10a was formed in a portion of the insulating film 10 that corresponded to the detecting unit $B_1$, thus avoiding a direct contact between the upper electroconductive member 3a and the sheet material P.

The insulating films 6 and 7 were each formed from silicon dioxide by RF sputtering to a thickness of 3 μm. The lower electroconductive member 3b was formed from Pt of 300 nm thicknesses by RF sputtering. A Ti film with a thickness of 50 nm was formed between the lower electroconductive member 3b and the insulating films 6 and 7. The metal oxide 4 was a PZT (Zr/Ti=36/65) film that was formed by MOCVD to a thickness of 5 μm and patterned by normal photolithography to have an area of 2 mm×5 mm. The electroconductive members 3a and 3b each had a width of 500 μm but, in the detecting unit $B_1$, had the meander structure as shown in the enlarged view of FIGS. 3B and 3C with the width set to 200 μm and the total length to 3 mm. The PZT 4 and the insulating film 7 have the same thickness in principle but a slight level difference at the interface between the two does not cause a problem.

Next, the method used to form the lower electroconductive member 3b was employed for formation of the upper electroconductive member 3a from Pt and then formation of a Ti film. The silicon oxide film 10 was formed to a thickness of 1 μm as a protective film of the electroconductive member 3a, and the meander structure portions of the electroconductive members alone were removed by etching. Lastly, the silicon substrate 5 was etched (see Symbol 5a) to hollow out the meander structure of the electroconductive members.

The media sensor $G_1$ was bonded to a side face of the impact member (external force applying unit) C as shown in FIG. 8. The impact member C was supported by an impact control unit F and was collided against the sheet material P using a not-shown spring. The media sensor $G_1$, the impact control unit F and the memory unit D were connected to the signal detecting/processing unit (judging unit) E, so that information of the sheet material P was obtained. The memory unit D stored sheet material information in advance, for example, the correlation between the temperature, the humidity, and an output signal of the sensor (voltage or the like). Though not shown in the drawing, the entire system may be controlled by an external control device such as a personal computer.

Copy paper FB 90 and FB 75 (Fox River Bond, a product of Fox River Paper Co.) and Xx 90 and Xx 105 (manufactured by XEROX CORPORATION) were used as sheet materials.

In this example, these sheet materials received an external force while being fixed vertically to a support base 20 as shown in FIG. 8. The impact member C used was formed from brass and weighed 3 g. The movement stroke of the impact member C was set to 1 mm or 4 mm.

Prior to actual detection of a sheet material, data was stored in the memory unit D by the following method:

The sheet identifying device $A_2$ was put in an environment-controlled test room where the temperature and the humidity were controlled; an experiment was performed 100 times on 10 sheets of each paper (sheet material), and the average voltage generated, the standard deviation, and the product number of the recording paper which were obtained through statistical work were stored in the memory unit D. During the measurement, the temperature was varied from 5° C. to 40° C. and the humidity was varied from 5% RH to 99% RH. After the temperature and the humidity were controlled to reach predetermined values, the sample was left to stand in the environment for 48 hours and then a dynamic force was applied to the sample to make measurements. When the temperature was 25° C., the humidity was 50% RH, and the movement stroke was set to 1 mm, the average voltage generated was 69 mV for FB 75, 58 mV for FB 90, 74 mV for Xx 75, and 68 mV for Xx 105. When the movement stroke was set to 4 mm, the average voltage generated was 158 mV for FB 75, 154 mV for FB 90, 167 mV for Xx 75, and 170 mV for Xx 105. The standard deviation of the voltage generated was 0.7 mV at maximum.

Thereafter, actual sheet detection was carried out using the following method.

A dynamic force was applied to the above four types of recording paper (hereinafter randomly denoted by $P_A$, $P_B$, $P_C$ and $P_D$) in a normal laboratory. When the movement stroke was set to 1 mm, the output upon impact from the sensor G1 that was fixed to the impact member C was 70 mV for $P_A$, 60 mV for $P_B$, 75 mV for $P_C$, and 69 mV for $P_D$. When the movement stroke was set to 4 mm, the sensor output upon impact was 160 mV for $P_A$, 155 mV for $P_B$, 168 mV for $P_C$, and 172 mV for $P_D$. The experiment result of the case when the movement stroke was 1 mm revealed that $P_B$ was FB 90 and that $P_C$ was Xx 90. The experiment result of the case when the movement stroke was 4 mm revealed that $P_A$ was FB 75 and that $P_D$ was Xx 105.

In the measurement described above, the temperature and humidity of the surroundings of each sheet material were measured immediately before the external force was applied. The results were checked against the data in the memory unit D to predict the voltage generated from each sheet material, and the predicted value was compared with the experiment result to use an error of 3 mV or less between the two as a guideline to determine the product number of the sheet material. The temperature was between 25.2° C. and 25.6° C. and the humidity was between 48% and 50% in the above measurement. The temperature and the humidity were determined by a change in electric resistance of the electroconductive members 3a and 3b.

Although the sensor $G_1$ was attached to a side face of the impact member C in this example, no limitation was put on where to attach the sensor $G_1$ as long as the sensor $G_1$ was attached directly to the impact member C.

Moreover, when the temperature and the humidity were changed artificially, setting the temperature to 30° C. and the humidity to 85% RH, for instance, voltage generation from each paper (sheet material) was reduced whereas increased voltage generation was observed at a temperature of 10° C. and a humidity of 15% RH. In such cases, application of two types of dynamic forces made it possible for the device to identify each recording paper.

EXAMPLE 3

Figure 10:
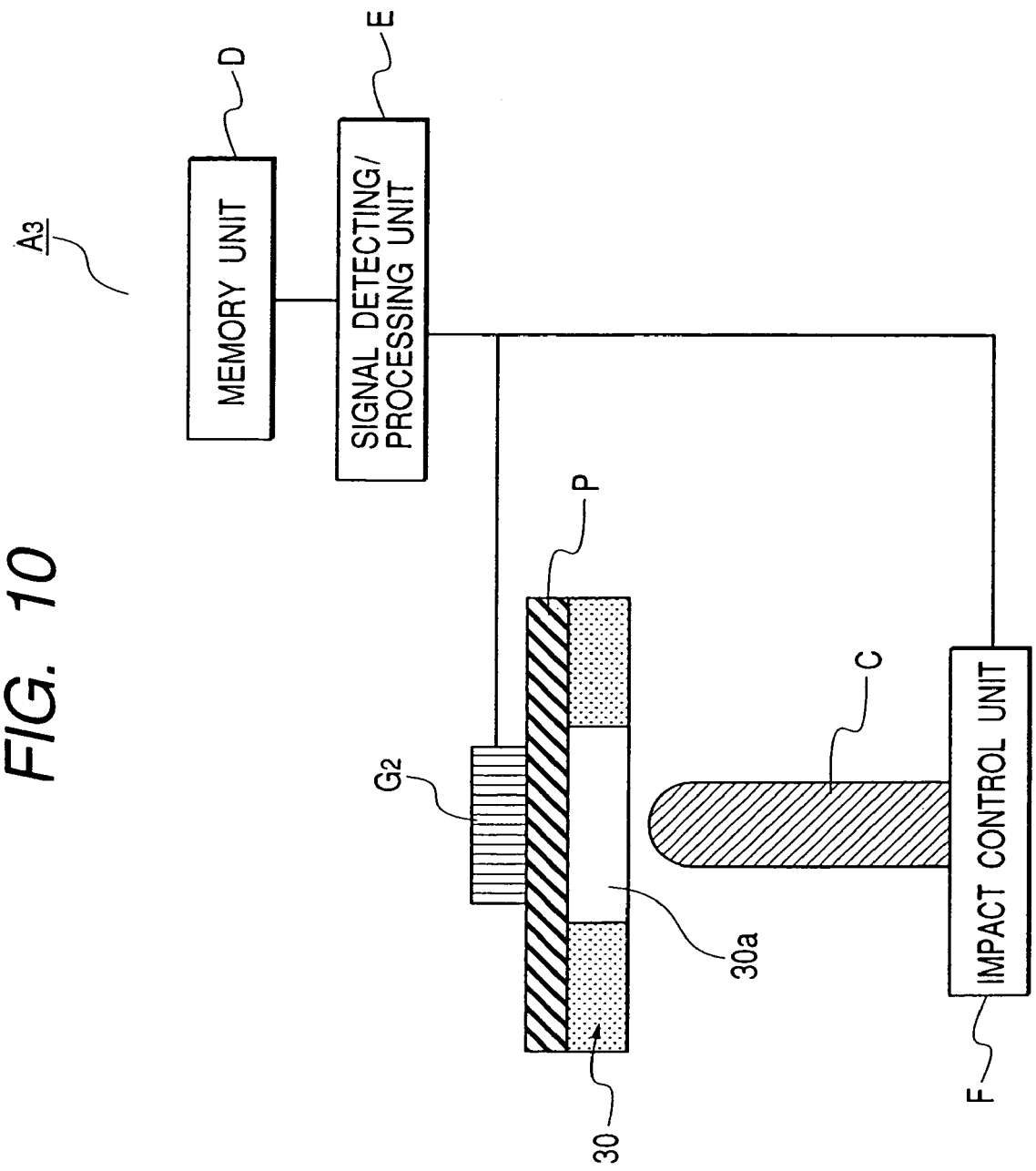
FIG. 10 is a sectional view showing an example of the structure of the device according to the present invention.

In this example, a sheet identifying device (information detecting device) $A_3$ shown in FIG. 10 was mounted to a copying machine (image forming apparatus).

The copying machine was equipped with: a sheet feeding cassette (first storage unit) for storing recording paper (a first sheet material); an image forming unit for forming an image on the recording paper; a paper transporting device (first sheet material transporting device) for transporting recording paper from the sheet feeding cassette to the image forming unit; an original table (second storage unit) on which an original (second sheet material) was placed; an image reading unit for reading an image of the original; an original transporting device (second sheet material transporting device) for transporting the original image to the image reading unit; an image control unit for controlling image formation conditions based on information from the sheet identifying device; and a sheet delivery tray (third storage unit) for storing recording paper on which an image was formed.

A sheet of recording paper was set in the sheet feeding cassette (see Step S11 in FIG. 7) and an original was set in the original table (Step S21). In this state, an operator performed a given operation such as depressing a switch button to start transportation of the original to the image reading unit, where an image of the original was read (Steps S22 and S23). Meanwhile the recording paper was transported to the image forming unit, where an image was formed on the recording paper (Steps S12, S13 and S14). Then the original and the recording paper were discharged (Steps S15 and S24).

As shown in FIG. 10, the sheet identifying device $A_3$ of this example had: a support base 30 which had a hole portion 30a and on which recording paper P was placed; an impact member (external force applying unit) C placed below the hole portion 30a while being supported by an impact control unit F; a media sensor $G_2$ placed above the hole portion 30a; a driving device (not shown in the drawing) for moving the media sensor $G_2$ up and down; a signal detecting/processing unit E; and a memory unit D. The media sensor $G_2$ was structured as shown in FIG. 3A, and was mounted to the copying machine such that an insulating film 10 faced toward the support base 30. The media sensor $G_2$ was placed in the vicinity of the image forming unit, and was moved to come into contact with recording paper transported to identify the recording paper.

Used as recording paper were FB 90 and FB 75 (Fox River Bond, a product of Fox River Paper Co.) and Xx 90 and Xx 105 (manufactured by XEROX CORPORATION). These are different from one another in thickness and surface roughness and, therefore, in laser beam printers, for example, different image forming conditions are chosen for different sheet materials. For instance, the above four types of recording paper are divided by image forming condition into three groups with FB 75 and FB 90 constituting one group, Xx 90 constituting another group, and Xx 105 constituting still another group.

The following method was employed to identify the recording paper:

The recording paper P was placed on the support base 30. In this state, the media sensor $G_2$ was brought into contact with the paper P and the impact control unit F drove the impact member to apply an impact force to the recording paper P.

A signal was outputted from the media sensor $G_2$, and the signal detecting/processing unit E compared the signal with the data in the memory unit D to determine the type of the paper and image formation conditions (including the toner fixing temperature). Based on the image formation conditions determined, the image control unit and the image forming unit formed an image.

The data stored in the memory unit D for each recording paper included the average voltage generated upon impact and the standard deviation of the voltage generated. According to the stored data, when the temperature was 25° C. and the humidity was 50% RH, the voltage generated upon impact that was applied from a 1 mm distance was 69 mV for FB 75, 58 mV for FB 90, 74 mV for Xx 75, and 68 mV for Xx 105. When an impact was applied from a 4 mm distance at the same temperature and humidity, the average voltage generated was 158 mV for FB 75, 154 mV for FB 90, 167 mV for Xx 75, and 170 mV for Xx 105. The standard deviation of the voltage generated was 0.7 mV at maximum.

In actual image formation, various kinds of recording paper were fed in random order. Upon application of impact from a 1 mm distance, the voltage generated was 69 mV for $P_A$, 60 mV for $P_B$, 75 mV for $P_C$, and 69 mV for $P_D$. Upon impact applied from a 4 mm distance, the voltage generated was 159 mV for $P_A$, 154 mV for $P_B$, 168 mV for $P_C$, and 171 mV for $P_D$. The temperature and humidity measured immediately before the impact was applied were between 25.0° C. and 25.2° C. and between 49.8% and 50.2% RH, respectively. The results were checked against the data in the memory unit D and the sheets $P_A$, $P_B$, $P_C$ and $P_D$ were identified as FB 75, FB 90, Xx 90 and Xx 105, respectively. Images were formed on $P_A$ and $P_B$ under the same image formation condition. Image formation conditions different from the one used for $P_A$ and $P_B$ were employed to form images on $P_C$ and $P_D$.

Figure 9:
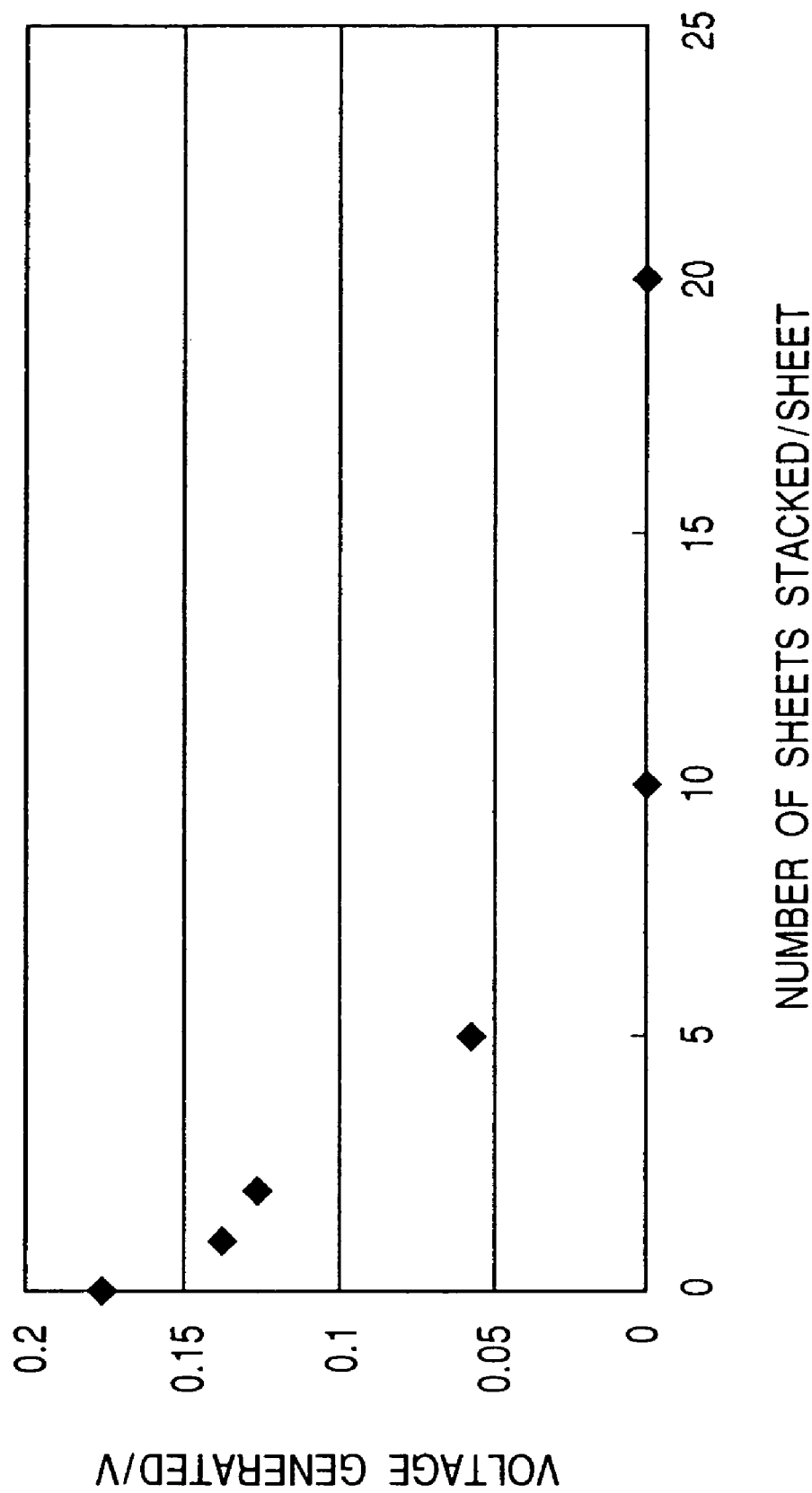
FIG. 9 is a waveform chart showing an example of an output signal of information obtaining means.

The media sensors $G_1$ and $G_2$ can be used to detect whether or not sheet materials stuck to one another are transported together (or the presence or absence of a sheet material). FIG. 9 shows voltage when the impact member C weighing 6 g was collided to the sheet material at a speed of 0.48 m/s with a spring (not shown) from a 1 mm distance. The sheet material used was LC 301 (a product of Canon Kabushiki Kaisha). As the graph shows clearly, the voltage generated is varied depending on the number of sheets stacked. Therefore it is possible to judge from the voltage generated how many sheets are piled up.

EXAMPLE 4

Figure 12:
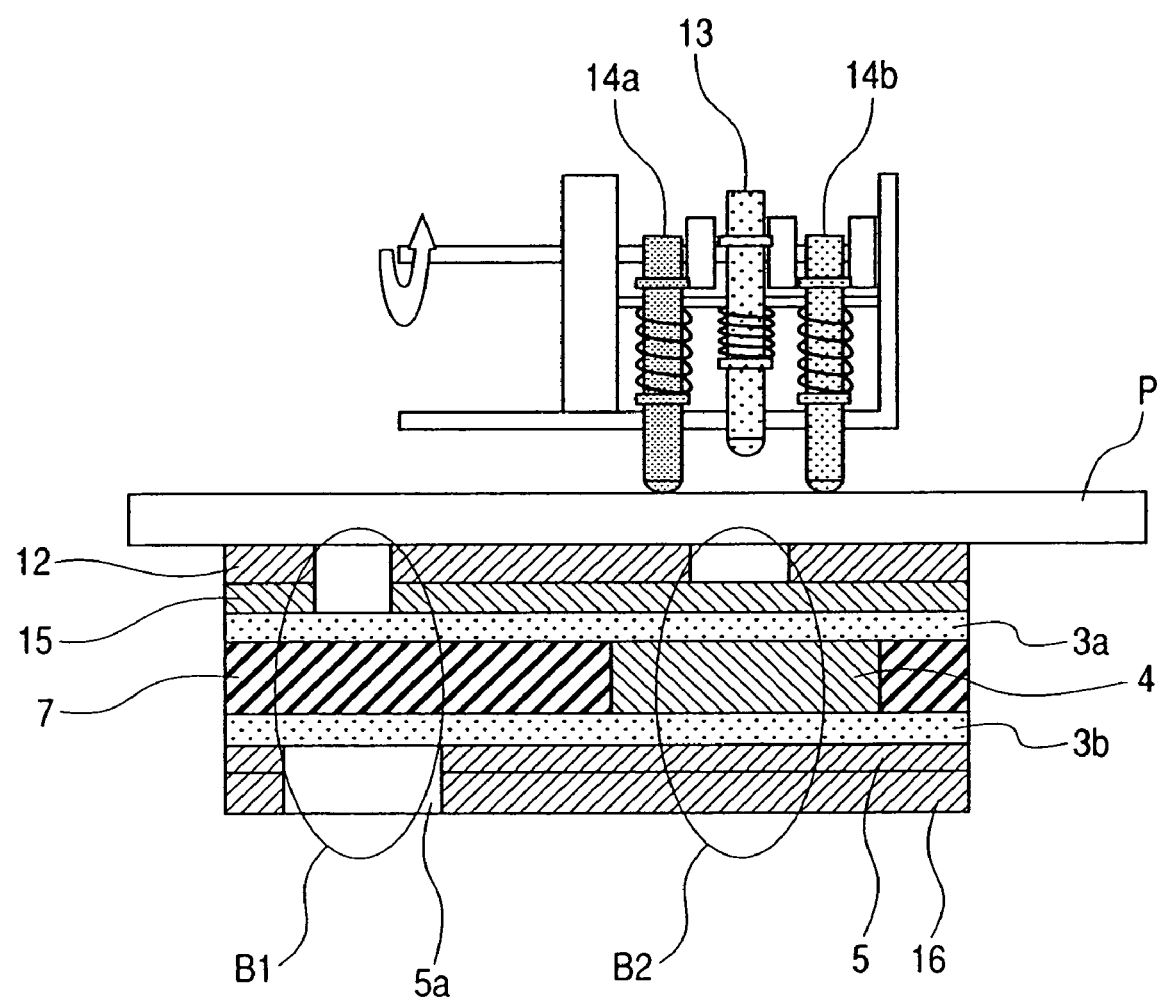
FIG. 12 is a sectional view showing a part of a structure of an information processing device according to the present invention.

FIG. 12 is a structural diagram showing the present invention in section. FIG. 12 only shows an external force applying unit and signal detecting units. In the external force applying unit, an impact applying member 13 and holding-down members 14a and 14b are attached to a rotary mechanism indicated by the rounded arrow in FIG. 12. The impact applying member 13 applies an external force to the sheet material P. The holding-down members 14a and 14b were hold-downed on a sheet material. The holding-down members are usually not in contact with a sheet material, and only come into contact with a sheet material immediately before an external force is applied to limit the movement of the sheet material until application of an external force is finished. The holding-down members and the impact applying member both utilize a spring. In the present invention, an external force was applied twice and the cam shape was set such that the intensity of the external force was varied between the first application and the second application.

Symbol 7 denotes an insulating member made from silicon dioxide. Symbol 4 denotes PbZrTiO3 (Zr/Ti=40/60). Symbols 3a and 3b denote an electroconductive member, respectively, having a two-layer structure of Pt/Ti and they are disposed such that Ti is in contact with 7 and 4. These were made by RF sputtering. 4 and 7 had a thickness of 5 µm. 3a and 3b have a meander structure with a thickness of 0.15 µm at B1 and have a thickness of 0.4 µm at the other portion. 12 and 15 each denote stainless sheet and have a thickness of 0.2 mm. Symbol 5 denotes a substrate made from silicon single crystal and was provided with a thermally oxidized film of silicon dioxide with a thickness of 0.1 μm at a portion contacting with 3b. Symbol 16 is a stainless sheet having a thickness of 3 mm. 12, 15 and 16 respectively were attached with an adhesive after a hole was made at a white portion with a mechanical processing.

The portion B1 in FIG. 12 shows a detecting unit for detecting an amount of moisture of the sheet material. The portion B2 in FIG. 12 shows an information obtaining means for obtaining information of the sheet material. The holes 12 and 15 in the portion B1 have an elliptic shape with a long diameter of 15 mm and a short diameter of 5 mm. The hole 5a is used for making smaller heat capacity of the portion B1 and was processed to a circular shape with a diameter of 4 mm.

Figure 13:
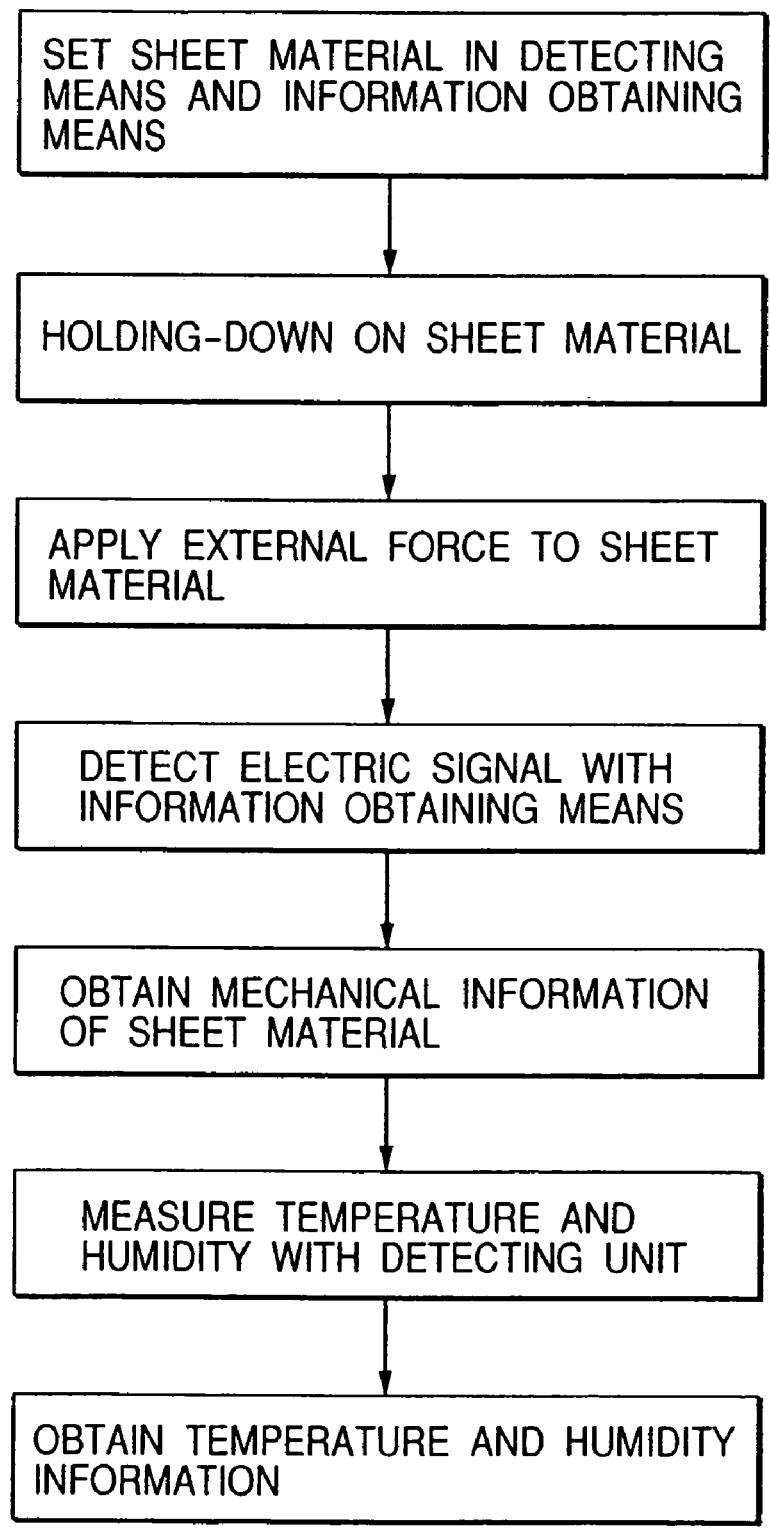
FIG. 13 is a flow chart illustrating an information detection procedure of the present invention.

An example of a procedure of obtaining sheet material information was shown in FIG. 13. First, a sheet material was set in a detecting unit (B1 in the drawing) and information obtaining means (B2 in the drawing). At this point, the sheet material may be still or in motion. Next, utilizing the force of the spring, the holding-down members 14a and 14b were brought into contact with the sheet material to bring a member 12 into contact with the sheet material. Thereafter an external force was applied to the sheet material by the external force applying member 13. As the sheet material was deformed until colliding against a bending impact receiving member 15, a voltage was generated in the information obtaining means (B2). Based on this voltage signal, mechanical information of the sheet material was obtained. The detecting unit (B1) then measured the temperature and the humidity. Thereafter, the sheet material was released from the hold of the holding-down members. A not-shown judging circuit identified the sheet material and the information was stored in a memory unit if necessary. The detecting units may be used as a normal temperature meter and hygrometer even without sheet materials, and the detecting unit and the information obtaining means may operate separately.

In the present invention, a sheet material is transported in a direction perpendicular to the surface of the drawing at a speed of 0 to 200 cm/s. The sheet holding-down members 14 were formed of stainless steel and weigh 4 g. Utilizing a spring, the sheet holding-down members 14 held down a sheet material with a force of about 12 gf. The external force applying unit 13 was formed of stainless steel, weighed 4 g, and applied an external force at a rate of 0.4 m/s and 0.2 m/s. The member 12 regulated the bent amount of a sheet material. Here a stainless steel plate with a thickness of 0.2 mm was used as the member 12. The tips of the external force applying member 13 and the sheet holding-down members 14 each had a radius of curvature of 3.5 mm and were each processed to have a 1 mm2 area flat surface. The member 15 may be integrated with the member 12. Here, the member 15 was a separate member and was a stainless steel plate with a thickness of 1 mm. The first detecting unit prevented mechanical damage to the piezoelectric element and at the same time transmitted a response of a sheet material to an external force to the second detecting unit. In the second detecting unit, an electroconductive member 3a was exposed in order to avoid lowering of detection responsiveness. A piezoelectric 4 was formed from Pb(Zr, Ti)03 to a thickness of 5 μm. The electroconductive member 3a and an electroconductive member 3b were both made of platinum, and a region of the electroconductive members that serves as the detecting unit B1 was processed to have a meander structure. A substrate 5 was formed of single crystal silicon. NBS-based rubber cushion was used for a member 16.

Figure 14:
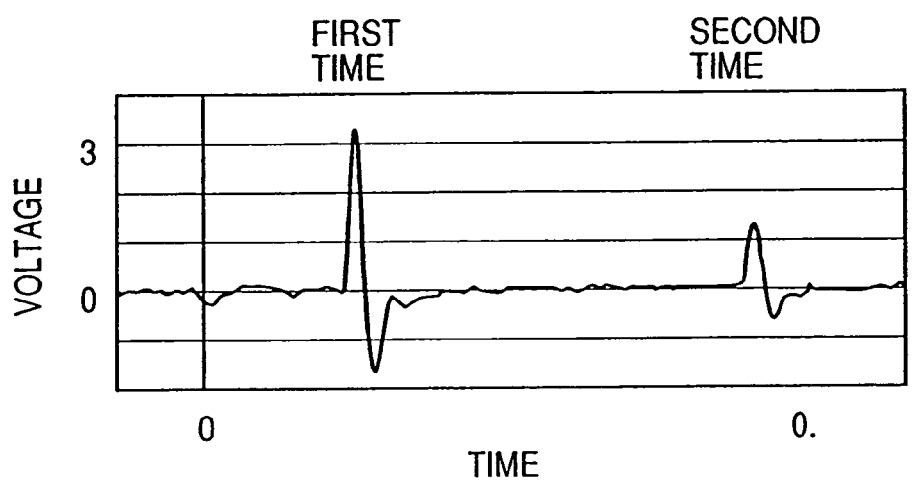
FIG. 14 is a diagram showing an example of an output signal of information obtaining means.
Figure 15:
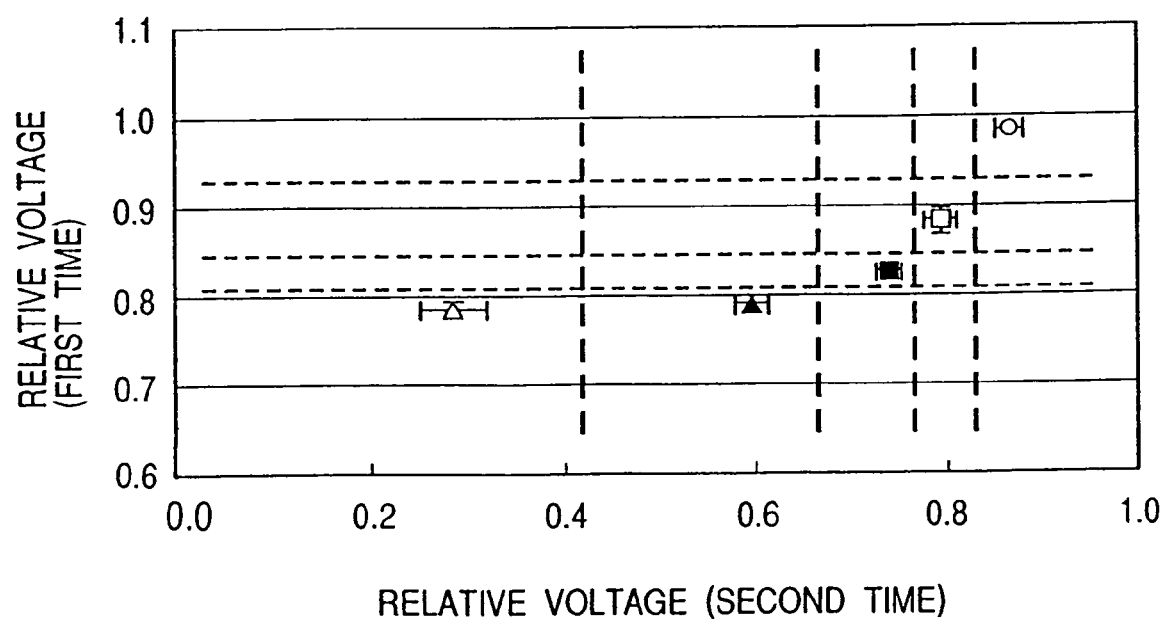
FIG. 15 is a diagram showing an example of a sheet material judging table of the present invention.

Employed as sheet materials were copy paper manufactured by Sumitomo 3M, XEROX CORPORATION, Fox River Paper Co., and Kimberly Clark Corporation. A measurement was made by the identifying device of the present invention while moving a sheet material at a rate of 20 cm/s. When the sheet holding-down members and the external force applying means were operated when a sheet material was not in place, an electric signal shown in FIG. 14 was obtained. In the graph of FIG. 14, the time count was started at the instant the sheet holding-down members came into contact with the member 12 (Time Zero). The voltage generated by an external force applied at a rate of 0.4 m/s (first application) was about 3.2 V (First Time in FIG. 14 (intense)) and the voltage generated by an external force applied next at a rate of 0.2 m/s (second application) was 1.3 V (Second Time (weak)). It took about 0.1 second from the second time voltage generation to removal of the sheet holding-down members. The next sheet material was set and a measurement was made in a similar manner. Although the voltage generated was varied from one sheet material type to another, the relative voltage value was obtained for the case of measuring each sheet material at a temperature of 23° C. (room temperature) and a humidity of 48% using as the reference the voltage of the case when a sheet material was not in place. The obtained relative voltage value is shown in FIG. 15. In FIG. 15, respective symbols show papers as follows.

○: CG 300 for monochrome laser printer manufactured by Sumitomo 3M Co.
□: Plain paper XEROX 4024 75 g/cm$^2$ manufactured by Xerox
Δ: Cardboard XEROX INDEX 90# 163 g/cm$^2$ manufactured by Xerox
■: Bond paper FOX RIVER BOND 75 g/cm$^2$ manufactured by FOXRIVER PAPER CO.
▲: Rough paper NEENAH CLASSIC LAID TEXT 105 g/cm manufactured by Kimberly-Clark Co.

The error bar in FIG. 15 indicates fluctuation of when the temperature and the humidity are changed. In the present invention, a measurement was made in three different temperature/humidity settings: 10° C./15%, 23° C./48%, and 30° C./80%. When the temperature/humidity setting is changed, the voltage generated is fluctuated irrespective of the presence or absence of a sheet material. However, the voltage fluctuation could be contained within a range of several % as shown in FIG. 15 by using the relative voltage for the case when a sheet material was not in place. Based on this data, the relative voltage threshold (indicated by a dotted line in FIG. 15) for identifying each sheet material was determined and stored in advance as an identification table in the memory unit. The memory unit stores necessary information such as physical properties of each paper, for example, product number, basic weight, density, paper thickness, Gurley stiffness, air permeability, coefficient of friction, and sheet material handling condition.

When measuring an unknown sheet material, the sheet material is identified by consulting the table of FIG. 15 and necessary information can be retrieved from the memory unit. Used here are 5 types of sheet materials, but the present invention is capable of identifying as many types of sheet materials as desired.

In addition, since the first and second detecting units can measure the temperature and humidity of the vicinity of a sheet material, it is possible to judge whether or not the temperature and the humidity are within the range stored in the memory unit. If the temperature and the humidity are within the range, necessary information can be retrieved from the memory unit. If outside the range, an operator may be alerted of this fact by a not-shown display device or processing may be carried out based on other stored information than FIG. 15.

The invention claimed is:

1. A device for identifying types of sheet materials, comprising:
   a detecting unit for detecting information regarding moisture of a sheet material;
   an external force applying unit for applying an external force to the sheet material;
   an information obtaining unit for obtaining information according to a force that is attenuated by the presence of the sheet material when the external force is applied to the sheet material by the external force applying unit, said detecting unit formed integrally with said information obtaining unit; and
   a judging unit for identifying the type of the sheet material based on the information obtained from the detecting unit and the information obtained from the information obtaining unit.

2. The device for identifying types of sheet materials according to claim 1, wherein the detecting unit detects information regarding moisture of at least one of the sheet material and atmospheric gas in the vicinity of the sheet material.

3. The device for identifying types of sheet materials according to claim 1, further comprising:
   a memory unit for storing information regarding moisture and mechanical properties of various sheet materials,
   wherein the type of a sheet material is identified based on detection results of the detecting unit and the information obtaining unit and data of the memory unit.

4. The device for identifying types of sheet materials according to claim 1, wherein the detecting unit has an electroconductive member and detects information regarding moisture of the sheet material or atmospheric gas from a change in electric resistivity of the electroconductive material.

5. The device for identifying types of sheet materials according to claim 1, wherein the information obtaining unit comprises a metal oxide, or a semiconductor, or an organic compound or an inorganic compound each having a piezoelectric characteristic, and electroconductive members, and detects a response of the sheet material to the external force based on a voltage change detected in the electroconductive members.

6. The device for identifying types of sheet materials according to claim 4, wherein the information obtaining unit has a plurality of electroconductive members and the electroconductive member of the detecting unit also serves as one of the electroconductive members of the information obtaining unit.

7. The device for identifying types of sheet materials according to claim 5,
   wherein the metal oxide, or the semiconductor, or the organic compound or the inorganic compound each having a piezoelectric characteristic is a ferroelectric, a pyroelectric, or a piezoelectric, and
   wherein the piezoelectric characteristic of the metal oxide, the semiconductor, or the organic compound or the inorganic compound is utilized to detect the response of the sheet material to the external force applied to the sheet material.

8. The device for identifying types of sheet materials according to claim 4,
   wherein a change in electric resistivity of the electroconductive member is measured by a first signal detecting unit for measuring electric resistivity of the electroconductive member,
   wherein the voltage change is measured by a second signal detecting unit for detecting electric signal generated between the electroconductive members, a pair of the electroconductive members being disposed so as to interpose a metal oxide, or a semiconductor, or an organic compound or an inorganic compound each having a piezoelectric characteristic, and
   wherein the type of a sheet material is judged based on signals from the first signal detecting unit and/or the second signal detecting unit.

9. The device for identifying types of sheet materials according to claim 1, wherein the external force is at least one of an impact force and an oscillation force.

10. The device for identifying types of sheet materials according to claim 3,
    wherein the external force applying unit has a contact member supported to move freely and come into contact with a sheet material, and a drive source for driving the contact member,
    wherein the information obtaining unit has an elastic member mounted to the contact member and a deformation amount sensor unit for detecting the deformation amount of the elastic member, and
    wherein the information obtaining unit detects a response of the sheet material based on the deformation amount of the elastic member which is detected by the deformation amount sensor unit when the contact member is driven by the drive source to collide against the sheet material.

11. The device for identifying types of sheet materials according to claim 1, wherein the detecting unit has a nicked portion.

* * * * *

UNITED STATES PATENT AND TRADEMARK OFFICE
CERTIFICATE OF CORRECTION

PATENT NO. : 7,239,817 B2
APPLICATION NO. : 10/535837
DATED : July 3, 2007
INVENTOR(S) : Norio Kaneko It is certified that error appears in the above-identified patent and that said Letters Patent is hereby corrected as shown below:

ON THE TITLE PAGE:
At Item (30), Foreign Application Priority Data, "Dec. 26, 2003 (WO) ....... PCT/JP03/16930" should be deleted.
At Item (56), References Cited, "ELectrical" should read --Electrical--.

COLUMN 2:
Line 35, "though 7." should read --through 7.--.

COLUMN 3:
Line 62, "zig-zag" should read --zigzag--.

COLUMN 4:
Line 32, "zig-zag" should read --zigzag--.

COLUMN 5:
Line 18, "represent" should read --represents--.

COLUMN 8:
Line 17, "forming-" should read --forming--.

COLUMN 9:
Line 59, "tip of thereof" should read --tip thereof--.

COLUMN 10:
Line 37, "lower" should read --electric resistance of the lower--.

COLUMN 11:
Line 20, "(Zr,Ti=36/65)" should read --(Zr,Ti=35/65)--.
Line 59, "used" should be deleted.

COLUMN 14:
Line 47, "hold-downed" should read --held down--.

COLUMN 15:
Line 60, "Pb(Zr,Ti)ɸ3" should read --Pb(Zr,Ti)03--.

UNITED STATES PATENT AND TRADEMARK OFFICE
CERTIFICATE OF CORRECTION

PATENT NO. : 7,239,817 B2
APPLICATION NO. : 10/535837
DATED : July 3, 2007
INVENTOR(S) : Norio Kaneko It is certified that error appears in the above-identified patent and that said Letters Patent is hereby corrected as shown below:

COLUMN 16:
Line 35, "FOXRIVER" should read --FOX RIVER--.

Signed and Sealed this

Fourth Day of December, 2007

JON W. DUDAS
*Director of the United States Patent and Trademark Office*